US00PP16940P2

(12) United States Plant Patent

Takamura

(10) Patent No.: US PP16,940 P2

(45) Date of Patent: Aug. 8, 2006

(54) *VERBENA* PLANT NAMED 'SUNTAPILAVEPI'

(50) Latin Name: *Verbena×hybrida*
Varietal Denomination: Suntapilavepi

(75) Inventor: Naoto Takamura, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 103 days.

(21) Appl. No.: 11/091,803

(22) Filed: Mar. 28, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—C. A. Whealy

(57) ABSTRACT

A new and distinct cultivar of *Verbena* plant named 'Suntapilavepi', characterized by its outwardly spreading and decumbent plant habit; freely branching and vigorous growth habit; light red purple-colored flowers; freely and continuous flowering habit; long-lasting flowers; non-fertile flowers; and good garden performance.

1 Drawing Sheet

Botanical designation: *Verbena×hybrida.*
Cultivar denomination: 'Suntapilavepi'.

BACKGROUND OF THE INVENTION

The present Invention relates to a new and distinct cultivar of *Verbena* plant, botanically known as *Verbena×hybrida,* and hereinafter referred to by the cultivar name Suntapilavepi.

The new *Verbena* is a product of a planned breeding program conducted by the Inventor in Higashiomi, Shiga, Japan. The objective of the breeding program was to create new *Verbena* cultivars with attractive flower coloration.

The new *Verbena* originated from a cross-pollination made by the Inventor in March, 1999 in Higashiomi, Shiga, Japan of a proprietary selection of *Verbena* sp. identified as code T86-99-2, not patented, as the female, or seed, parent with a proprietary selection of *Verbena×hybrida* identified as code number T85-99-2, not patented, as the male, or pollen, parent. The new *Verbena* was discovered and selected by the Inventor as a flowering plant within the progeny of the stated cross-pollination in a controlled environment in Higashiomi, Shiga, Japan.

Asexual reproduction of the new cultivar by terminal cuttings at Higashiomi, Shiga, Japan since October, 2001, has shown that the unique features of this new *Verbena* are stable and reproduced true to type in successive generations.

SUMMARY OF THE INVENTION

Plants of the cultivar Suntapilavepi have not been observed under all possible environmental conditions. The phenotype may vary somewhat with variations in environment such as temperature and light level without, however, any variance in genotype.

The following traits have been repeatedly observed and are determined to be the unique characteristics of 'Suntapilavepi'. These characteristics in combination distinguish 'Suntapilavepi' as a new and distinct cultivar of *Verbena:*

1. Outwardly spreading and decumbent plant habit.
2. Freely branching and vigorous growth habit.
3. Light red purple-colored flowers.

4. Freely and continuous flowering habit.
5. Long-lasting flowers.
6. Non-fertile flowers.
7. Good garden performance.

Plants of the new *Verbena* can be compared to plants of the female parent selection. In side-by-side comparisons conducted in Higashiomi, Shiga, Japan, plants of the new *Verbena* differed from plants of the female parent selection in the following characteristics:

1. Plants of the new *Verbena* had shorter lateral branches than plants of the female parent selection.
2. Plants of the new *Verbena* and the female parent selection differed in petal coloration as plants of the female parent selection had purplish white-colored petals.

Plants of the new *Verbena* can be compared to plants of the male parent selection. In side-by-side comparisons conducted in Higashiomi, Shiga, Japan, plants of the new *Verbena* differed from plants of the male parent selection in the following characteristics:

1. Plants of the new *Verbena* had shorter lateral branches than plants of the male parent selection.
2. Plants of the new *Verbena* and the male parent selection differed in petal coloration as plants of the male parent selection had light blue-colored petals.

Plants of the new *Verbena* can also be compared to plants of the *Verbena* cultivar Sunmaref TP-L, disclosed in U.S. Plant Pat. No. 9,121. In side-by-side comparisons conducted in Higashiomi, Shiga, Japan, plants of the new *Verbena* differed from plants of the cultivar Sunmaref TP-L in the following characteristics:

1. Plants of the new *Verbena* were smaller than plants of the cultivar Sunmaref TP-L.
2. Plants of the new *Verbena* had shorter internodes than plants of the cultivar Sunmaref TP-L.
3. Plants of the new *Verbena* had larger leaves than plants of the cultivar Sunmaref TP-L.
4. Plants of the new *Verbena* had taller inflorescences than plants of the cultivar Sunmaref TP-L.

5. Plants of the new *Verbena* and the cultivar Sunmaref TP-L differed in petal coloration as plants of the cultivar Sunmaref TP-L had purple violet-colored petals.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Verbena*.

The photograph at the top of the sheet is a side perspective view of a typical plant of 'Suntapilavepi'.

The photograph at the bottom of the sheet is a close-up view of typical flowers of 'Suntapilavepi'.

DETAILED BOTANICAL DESCRIPTION

The aforementioned photographs, following observations and measurements describe plants grown in Higashiomi, Shiga, Japan during the spring and summer in an outdoor nursery and under commercial production practices. Plants were grown in 15-cm containers and were about four months old when the photographs and description were taken. During the production of the plants, day temperatures averaged 23° C. and night temperatures averaged 15° C. Plants were pinched one time in the early spring. In the following description, color references are made to The Royal Horticultural Society Colour Chart, 2001 Edition, except where general terms of ordinary dictionary significance are used.

Botanical classification: *Verbena×hybrida* cultivar Suntapilavepi.

Parentage:

*Female, or seed, parent.*—Proprietary selection of *Verbena×hybrida* identified as code T86-99-2, not patented.

*Male, or pollen, parent.*—Proprietary selection of *Verbena×hybrida* identified as code T85-99-2, not patented.

Propagation:

*Type.*—By terminal cuttings.

*Time to initiate roots.*—About 10 to 14 days at 15 to 20° C.

*Time to produce a rooted plant.*—About one month at 15 to 20° C.

*Root description.*—Fine, fibrous, fleshy; ivory to pale brown in color.

*Rooting habit.*—Freely branching.

Plant description:

*Plant form/habit.*—Outwardly spreading and decumbent plant habit; broadly inverted triangle; vigorous growth habit. Freely branching habit with short internodes, dense and bushy growth habit.

*Plant height.*—About 11.8 cm.

*Plant width (spread).*—About 50 cm.

*Lateral branches.*—Length: About 25 cm. Diameter: About 1.2 mm. Internode length: About 3.1 cm. Strength: Strong. Texture: Pubescent. Color: 144B.

*Foliage description.*—Arrangement: Opposite, simple. Length: About 2.9 cm. Width: About 1.9 cm. Shape: Broadly angular-ovate. Apex: Acute. Base: Cuneate. Margin: Deeply pinnately parted. Texture, upper and lower surfaces: Pubescent. Venation pattern: Pinnate; reticulate. Color: Developing and fully expanded leaves, upper surface: 137B; venation, similar to lamina. Developing and fully expanded leaves, lower surface: 138B; venation, similar to lamina. Petiole: Length: About 1 cm. Diameter: About 1.4 mm. Texture: Pubescent. Color: 144C.

Flower description:

*Flower type/habit.*—Single, star-shaped salverform flowers arranged in terminal corymbs; flowers face mostly upright. Freely flowering habit with about 15 open flowers per inflorescence.

*Fragrance.*—None detected.

*Natural flowering season.*—Continuously flowering from April to November in Japan. Flowers not persistent.

*Postproduction longevity.*—Long-lasting; flowers last about one week on the plant.

*Inflorescence height.*—About 8.5 cm.

*Inflorescence diameter.*—About 4.3 cm.

*Flower buds.*—Height: About 1.1 cm. Diameter: About 1 mm. Shape: Cylindrical. Color: 73A.

*Flowers.*—Diameter: About 1.5 cm. Depth: About 1.4 cm. Tube diameter: About 1.5 mm. Tube length: About 1.1 cm.

*Petals.*—Quantity per flower: Typically five in a single whorl; petals fused at the base into a narrow tube. Lobe length: About 6.5 cm. Lobe width: About 6.4 mm. Shape: Cordate. Apex: Emarginate. Margin: Entire. Aspect: Mostly flat. Texture, upper and lower surfaces: Smooth, glabrous; satiny. Color: Developing and fully expanded petals, upper surface: N66D. Developing and fully expanded petals, lower surface: 75B. Throat: Close to N66D. Tube: N77D.

*Sepals.*—Quantity per flower: Typically five in a single whorl, fused; narrow tubular calyx. Length: About 9 mm. Width: About 1.2 mm. Shape: Lanceolate. Apex: Acute. Texture, upper and lower surfaces: Smooth, glabrous. Color, immature, upper and lower surfaces: 144B. Color, mature, upper and lower surfaces: 144B.

*Pedicels.*—Length: About 7.1 cm. Diameter: About 1.8 mm. Texture: Pubescent. Color: 144B.

*Reproductive organs.*—Stamens: Quantity per flower: Typically four. Anther shape: Ovoid. Anther length: Less than 1 mm. Anther color: 150A. Pollen amount: Moderate. Pollen color: 1B. Pistils: Quantity per flower: Typically one. Pistil length: About 1.5 cm. Stigma shape: Bi-parted. Stigma color: Close to 144A. Style length: About 1.3 cm. Style color: Close to 144B. Ovary color: 144B.

*Seed/fruit.*—Seed and fruit development have not been observed.

Disease/pest resistance: Plants of the new *Verbena* have not been noted to be resistant to specific pathogens and pests common to *Verbena*.

Garden performance: Plants of the new *Verbena* have been observed to have good garden performance and tolerate rain, wind and tolerated temperatures from 0 to 35° C.

It is claimed:

1. A new and distinct cultivar of *Verbena* plant named 'Suntapilavepi', as illustrated and described.

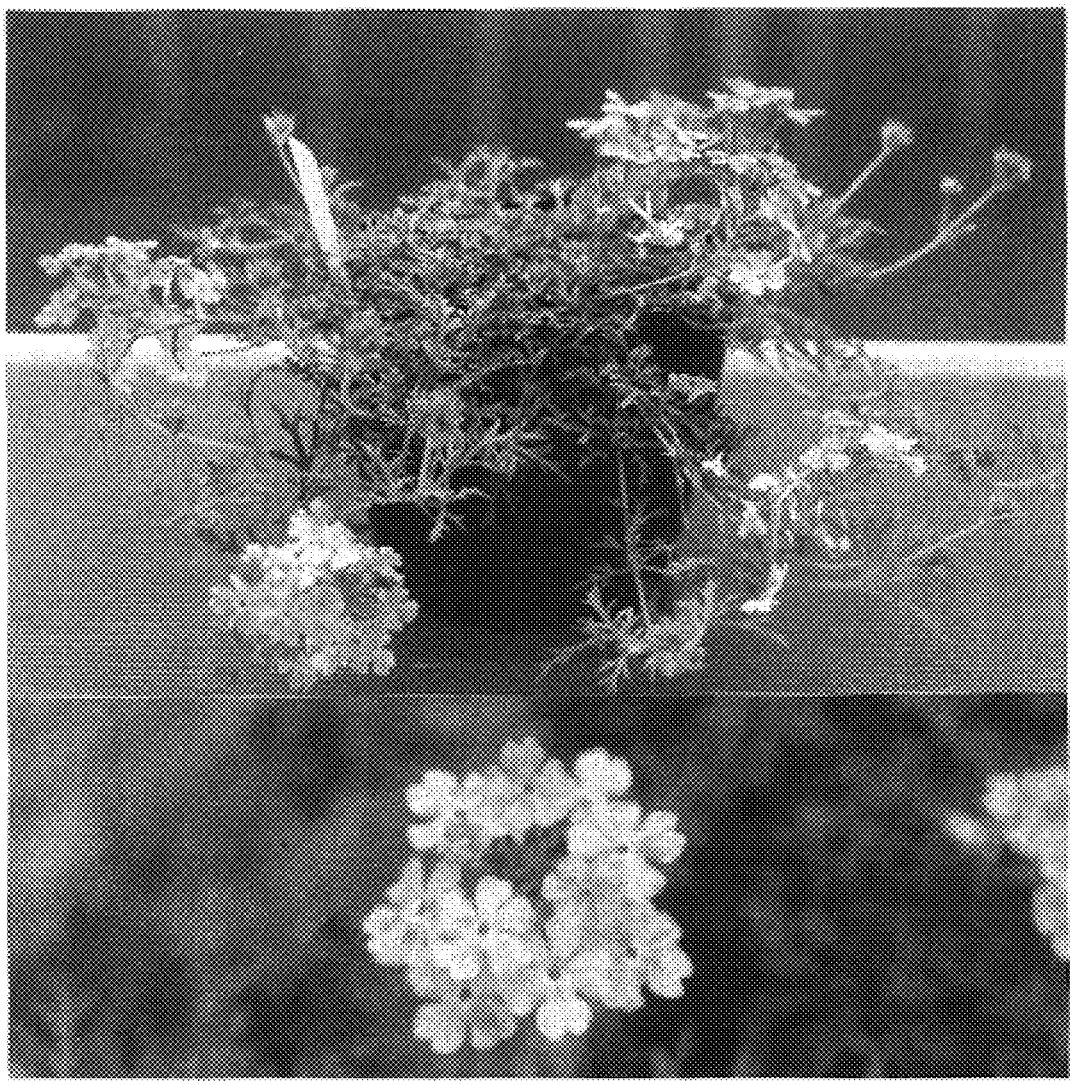

* * * * *